US005696262A

United States Patent [19]

Fuso et al.

[11] Patent Number: 5,696,262
[45] Date of Patent: *Dec. 9, 1997

[54] WATER-SOLUBLE TRIAZINES

[75] Inventors: Francesco Fuso, Therwil; Gerhard Reinert, Allschwil, both of Switzerland

[73] Assignee: Ciba Specialty Chemicals Corporation, Tarrytown, N.Y.

[ * ] Notice: The term of this patent shall not extend beyond the expiration date of Pat. No. 5,281,707.

[21] Appl. No.: 517,861

[22] Filed: Aug. 22, 1995

[30] Foreign Application Priority Data

Aug. 25, 1994 [CH] Switzerland ............................ 2606/94

[51] Int. Cl.$^6$ ............................................. C07D 401/12
[52] U.S. Cl. ...................... 544/212; 544/180; 544/198; 544/209; 544/218
[58] Field of Search ................................ 544/180, 209, 544/212, 218, 198

[56] References Cited

U.S. PATENT DOCUMENTS

| | | | |
|---|---|---|---|
| 4,161,592 | 7/1979 | Evans et al. | 544/198 |
| 5,181,935 | 1/1993 | Reinert et al. | 8/442 |
| 5,281,707 | 1/1994 | Fuso et al. | 544/212 |

FOREIGN PATENT DOCUMENTS

| | | |
|---|---|---|
| 0094048 | 11/1983 | European Pat. Off. . |
| 0209126 | 1/1987 | European Pat. Off. . |
| 0209127 | 1/1987 | European Pat. Off. . |
| 0389428 | 9/1990 | European Pat. Off. . |
| 2730449 | 1/1978 | Germany . |

OTHER PUBLICATIONS

Borzatta et al., Sem. Org. Synth. Summer Sch., "A. Corbella", 18th, pp. 135–153 (1993).
A. Valet, Paint India, vol. 42, No. 7, Jul. 1992, pp. 35–39 (particularly 35, right column, lines 11–14) HALS Light Stabilizers: "New Developments".

*Primary Examiner*—Yogendra N. Gupta
*Attorney, Agent, or Firm*—Kevin T. Mansfield; David R. Crichton

[57] ABSTRACT

The invention relates to novel water-soluble triazines of formula wherein the variables are as defined in the claims, to a process for their preparation and to the use thereof for the photochemical and thermal stabilisation of dyed or undyed polyamide fiber materials.

8 Claims, No Drawings

WATER-SOLUBLE TRIAZINES

The present invention relates to novel water-soluble triazines, to a process for their preparation and to the use thereof for the photochemical and thermal stabilisation of dyed or undyed polyamide fibre materials.

In EP-A-0 466 647 or EP-A-0 459 950 it is taught to stabilise polyamide fibres photochemically and thermally by treating them with specific compounds of the class of sterically hindered amines, so-called "HALS" stabilisers. It has been found, however, that the stabilisation thereby achieved does not in all respects meet the exacting demands made of it. There is therefore a need to provide compounds that afford polyamide fibre materials better protection against the action of light and heat.

It has now been found that it is possible to achieve enhanced stabilisation of polyamide fibre materials with the special triazines described hereinafter.

The novel water-soluble triazines are distinguished by particularly good fibre-affinity and good exhaustion, especially in the neutral pH range.

Accordingly, the invention relates to novel water-soluble triazines of the general formula

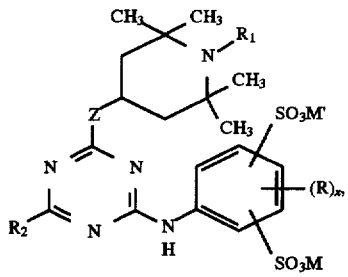

(1)

wherein

R is hydrogen, hydroxy; halogen; unsubstituted or carboxy-substituted $C_1-C_5$alkyl; $C_1-C_5$alkoxy; $C_1-C_5$alkanoyl; benzoyl; mono- or di-$C_5-C_5$alkanoylamino; carboxy; carbamoyl or an unsubstituted or a $C_1-C_5$alkyl- or halogen-substituted phenylsulfonyl, phenoxy, phenylthio or styryl radical;

$R_1$ is hydrogen; oxyl; hydroxy; $C_1-C_5$alkyl; $C_2-C_5$alkenyl; $C_1-C_5$alkoxy; $C_1-C_5$alkanoyl; benzoyl or benzyl;

$R_2$ is halogen; unsubstituted or phenyl-substituted $C_{1-C5}$alkyl; unsubstituted or $C_2-C_5$alkenyl-, phenyl- or diphenyl-$C_1-C_5$alkyl-substituted amino in which the phenyl moiety may be further substituted by halogen, cyano, nitro, trifluoromethyl, amino, mono- or di-$C_1-C_5$alkylamino, carbamoylamino, $C_1-C_5$alkylsulfonyl, unsubstituted sulfamoyl or sulfamoyl which is N-substituted by $C_1-C_5$alkyl, $C_1-C_5$hydroxyalkyl, phenyl or tolyl, unsubstituted or hydroxy- or carboxy-substituted $C_1-C_5$alkyl, unsubstituted or hydroxy- or $C_1-C_5$alkoxy-substituted-$C_1-C_5$alkoxy, $C_1-C_5$alkanoyl, benzoyl, mono- or di-$C_1-C_5$alkanoylamino, carboxy, carbamoyl, $C_1-C_5$alkoxycarbonyl or an unsubstituted or a halogen- or $C_1-C_5$alkyl-substituted phenylsulfonyl, phenoxy, phenylthio or styryl radical; unsubstituted or hydroxy- or carboxy-substituted mono- or di-$C_1-C_5$alkylamino in which the alkyl chain may be interrupted by an oxygen atom; unsubstituted or $C_1-C_5$alkyl-substituted mono- or di-$C_4-C_8$cycloalkylamino; unsubstituted or phenyl-substituted $C_1-C_5$alkoxy; $C_2-C_5$alkenyl; $C_2-C_5$alkenyloxy; $C_4-C_8$cycloalkoxy; unsubstituted phenoxy or phenoxy which is substituted by halogen, $C_1-C_5$alkyl, carboxy-$C_1-C_5$alkyl, $C_1-C_5$alkoxy, carboxy, carbamoyl, $C_1-C_5$alkanoyl, benzoyl, hydroxy, mono- or di-$C_1-C_5$alkanoylamino, or by an unsubstituted or a halogen-substituted phenylsulfonyl, phenoxy, phenylthio or styryl radical; $C_4-C_8$cycloalkoxy; phenyl; phenylthio; phenyl-$C_1-C_5$alkylthio; $C_1-C_5$alkylthio; $C_4-C_8$cycloalkylthio; unsubstituted or hydroxy-, $C_1-C_5$alkyl or carboxy-substituted 1-azacycloalkyl; unsubstituted or $C_1-C_5$alkyl-substituted morpholino or a radical of formula

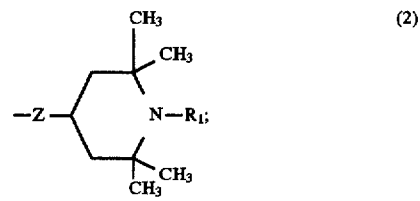

(2)

Z is —O— or —(NR$_3$)—, wherein $R_3$ is hydrogen or $C_1-C_5$alkyl;

M and M' are each independently of the other hydrogen, an alkali metal cation, an alkaline earth metal cation or an ammonium cation or an organic ammonium cation of formula $(C_1-C_4alkyl)_n(H)_mN^+$;

m is 0 to 3;

n is 1 to 4; and the sum of m+n=4, and x is 1 or 2.

R defined as halogen is typically fluoro, bromo and, preferably, chloro.

R defined as $C_1-C_5$alkyl is typically methyl, ethyl, n-propyl, isopropyl, n-butyl, isobutyl, sec-butyl, tert-butyl, amyl or isoamyl.

R defined as $C_1-C_5$alkoxy is typically methoxy, ethoxy, isopropoxy, isobutoxy, tert-butoxy or tert-amyloxy.

R defined as $C_1-C_5$alkanoyl is typically formyl, acetyl, propionyl or n-butyryl.

$R_1$ defined as $C_1-C_5$alkyl is typically methyl, ethyl, n-propyl, isopropyl, n-butyl, isobutyl, sec-butyl, tert-butyl, amyl or isoamyl.

$R_1$ defined as $C_1-C_5$alkoxy is typically methoxy, ethoxy, isopropoxy, isobutoxy, tert-butoxy or tert-amyloxy.

$R_1$ defined as $C_1-C_5$alkanoyl is typically formyl, acetyl, propionyl or n-butyryl.

$R_1$ defined as $C_2-C_5$alkenyl is typically vinyl, butenyl or, preferably, allyl.

$R_1$ defined as oxyl will be taken to mean an oxygen radical bonded to the nitrogen atom.

$R_2$ defined as halogen will typically be fluoro, bromo and, preferably, chloro.

$R_2$ defined as $C_1-C_5$alkyl is typically methyl, ethyl, n-propyl, isopropyl, n-butyl, isobutyl, sec-butyl, tert-butyl, amyl or isoamyl.

$R_2$ defined as $C_1-C_5$alkoxy is typically methoxy, ethoxy, isopropoxy, isobutoxy, tert-butoxy or tert-amyloxy.

$R_2$ defined as $C_1-C_5$alkanoyl is typically formyl, acetyl, propionyl or n-butyryl.

$R_2$ defined as $C_1-C_5$alkylthio is typically methylthio, ethylthio, propylthio or butylthio.

Illustrative examples of $R_2$ defined as mono- and di-$C_1-C_5$alkylamino typically include N-methylamino, N,N-dimethylamino, N-ethylamino, N,N-diethylamino, N,N-dipropylamino or N-methyl-N-ethylamino.

Illustrative examples of $R_2$ defined as mono-or di-$C_1-C_5$alkanoylamino typically include formylamino, acetylamino, propionylamino, butyrylamino, diformylamino, diacetylamino, dipropionylamino, dibutyrylamino or formylacetylamino.

$R_2$ defined as $C_4-C_8$cycloalkyloxy is typically cyclobutoxy, cyclopentoxy, methylcyclohexyloxy, ethylcyclohexyloxy, cycloheptyloxy, cyclooctyloxy or, preferably, cyclohexyloxy.

$R_2$ defined as mono- or di-$C_4$-$C_8$cycloalkylamino is typically monocyclohexylamino or, preferably, dicyclohexylamino.

$R_2$ defined as $C_4$-$C_8$cycloalkylthio is typically cycloheptylthio or, preferably, cyclohexylthio.

$R_2$ defined as $C_2$-$C_5$alkenyl, $C_2$-$C_5$alkenyloxy, mono- or di-$C_2$-$C_5$alkenylamino will typically be vinyl, butenyl, allyl, butenyloxy, allyloxy, monobutenylamino, monoallylamino, diallylamino or dibutylamino. Preferred radicals are allyl, allyloxy, monoallylamino and diallylamino. Allyl is particularly preferred.

$R_2$ defined as phenyl-$C_1$-$C_5$alkyl will typically be phenethyl, phenylpropyl, phenylbutyl or, preferably, benzyl.

$R_2$ defined as 1-azacycloalkyl is typically 1-pyrrolidyl or piperidino.

$R_2$ defined as phenyl-$C_1$-$C_5$alkoxy, mono- or bis(phenyl-$C_1$-$C_5$alkyl)amino and phenyl-$C_1$-$C_5$alkylthio is exemplified by phenylmethoxy, phenylethoxy, phenylpropoxy, monobenzylamino, monophenethylamino, dibenzylamino, diphenethylamino, benzylphenethylamino, benzylthio or phenethylthio.

$R_2$ defined as carboxy-$C_1$-$C_5$alkyl is exemplified by carboxymethyl, carboxyethyl, carboxypropyl, carboxyisopropyl, carboxybutyl, carboxyisobutyl, carboxy-sec-butyl, carboxy-tert-butyl, carboxyamyl or carboxyisoamyl.

Typical examples of alkali metal ions M and M' are the lithium, sodium or potassium cation. The sodium cation is preferred. Typical examples of alkaline earth metal ions are calcium and magnesium cations.

M or M' as ammonium cation of formula $(C_1-C_4alkyl)_n(H)_mN^+$ is suitably trimethylammonium or, preferably, triethylammonium.

Particularly interesting water-soluble triazines are those in which Z in formula (1) is —(NR$_3$)—.

Further water-soluble triazines of particular interest are those in which R in formula (1) is hydrogen, halogen, hydroxy or $C_1$-$C_5$alkyl.

Particularly interesting water-soluble triazines are also those in which $R_1$ in formula (1) is hydrogen or $C_1$-$C_5$alkyl.

Preferred compounds are also those wherein $R_2$ in formula (1) is mono-$C_1$-$C_5$alkylamino, di-$C_1$-$C_5$alkylamino, phenyl-$C_1$-$C_5$alkylamino, cycloalkylamino and phenylamino.

Particularly preferred compounds are those in which the two substituents —SO$_3$M and —SO$_3$M' in formula (1) are located at the benzene ring in positions 2 and 5 relative to the amino group.

Very particularly preferred compounds of formula (1) are those wherein R is hydrogen, halogen, hydroxy or $C_1$-$C_5$alkyl, $R_1$ is hydrogen or $C_1$-$C_5$alkyl, $R_2$ is a radical of formula (3), mono-$C_1$-$C_5$alkylamino, di-$C_1$-$C_5$alkylamino, phenyl-$C_1$-$C_5$alkylamino, cycloalkylamino or phenylamino which is unsubstituted or substituted in the phenyl moiety by $C_1$-$C_5$alkyl, and Z is —(NR$_3$)—, and the two substituents —SO$_3$M and —SO$_3$M' are located at the benzene ring in positions 2 and 5 relative to the amino group.

The invention also relates to the process for the preparation of the novel triazines of formula (1).

The water-soluble triazines of formula (1) can be prepared in different ways. The starting compound is usually a 2,4,6-trihalo-s-triazine. In those cases where $R_2$ is $C_1$-$C_5$alkyl or phenyl, it is convenient to start from 2,4-dihalo-6-$C_1$-$C_5$alkyl-s-triazine or 2,4-dihalo-6-phenyl-s-triazine.

The novel water-soluble triazines of formula (1) can conveniently be prepared by reacting 1 mol of a 2,4,6-trihalo-s-triazine, in succession, with 1 mol of the compound of formula

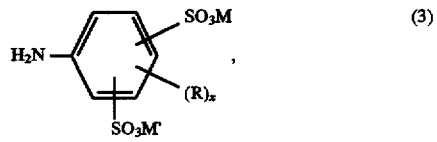

(3)

wherein M, M', Z, R and x are as defined in connection with formula (1), and with 1 or 2 mol of the piperidine of formula

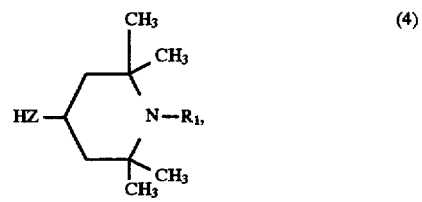

(4)

wherein $R_1$ and Z are as defined with respect to formula (1) and, if only 1 mol of the piperidine of formula (4) is used, with 1 mol of a $C_1$-$C_5$alkanolate, cycloalkanolate, phenolate, $C_1$-$C_5$alkylthiolate, cycloalkylthiolate or a phenylthiolate, a mono-$C_1$-$C_5$alkylamine, di-$C_1$-$C_5$alkylamine, cycloalkylamine, phenylamine, a 1-azacycloalkyl or morpholino compound, the sequence of the individual reaction steps being in any order. The usual procedure is that, in the first reaction step, the 2,4,6-trihalo-s-triazine is reacted with the compound having the lowest reactivity.

The reaction temperature is in the range from 0° to 100° C., preferably from 20° to 80° C., and the reaction time is from 1 to 20 hours, preferably from 1 to 4 hours.

The hydrohalic acid generated in the condensation reaction can be neutralised by the final product itself or by addition of a further base, typically aqueous ammonia, an alkali metal hydroxide, an alkali metal carbonate or hydrogen carbonate or an organic base such as triethylamine. The preferred base is an alkali metal carbonate such as sodium carbonate.

The reactions are conveniently carried out in aqueous solution without the addition of organic solvents. The starting 2,4,6-trihalo-s-triazines are known compounds. They are preferably used in the form of aqueous suspensions. A particularly preferred starting compound is cyanuric chloride. The other starting compounds used for the preparation of the compounds of formula (1), typically the compounds of formulae (3) or (4), are likewise known compounds.

All compounds of formula (1) are preferably prepared as sodium salts, conveniently by dissolving them in e.g. the equivalent amount of sodium hydroxide solution and formulating them to solutions, dispersions or emulsions for application.

The novel water-soluble triazines of formula (1) are suitable for enhancing the photochemical and thermal stability of undyed and dyed polyamide fibre materials. The use of the novel compounds for enhancing the photochemical and thermal stability of undyed and dyed polyamide fibre materials accordingly constitutes a further object of the present invention.

The novel compounds are representatives of the sterically hindered amines (HALS stabilisers) and can be integrated into standard textile finishing processes for polyamide fibres.

The compounds of formula (1) are applied in the practice of this invention from an aqueous bath which contains the compounds in an amount of 0.005 to 10% by weight, preferably of 0.05 to 2% by weight. The compounds are preferably added to the dyebath. Application can be made before, during or after dyeing by an exhaust or continuous process. Application during dyeing is preferred.

In the exhaust process, the liquor ratio can vary over a wide range, e.g. from 1:5 to 1:300, preferably from 1:10 to 1:50. The process is conveniently carried out in the temperature range from 30° to 130° C., preferably from 50° to 110° C.

In the continuous process the liquor is conveniently applied to a pick-up of 30–400% by weight, preferably of 70 to 250% by weight. The known and novel compounds are fixed on the fibre material by subjecting the material to a heat treatment. The fixation process can also be carried out by the cold pad-batch method.

The heat treatment is preferably carried out by treatment in a steamer with steam or superheated steam in the temperature range from 98° to 105° C. for conveniently 1 to 7, preferably 1 to 5, minutes. The fixation of the dyes and the compounds of formula (1) by the cold pad-batch method can be effected by storing the impregnated and preferably rolled up goods at room temperature (15° to 30° C.), suitably for 3 to 24 hours, the cold batching time depending naturally on the type of dye to be used.

When the dyeing process and fixation are complete, the dyeings are washed off and dried in conventional manner.

The dyed or undyed polyamide fibre materials obtained by the process of this invention have good photochemical and thermal stability.

The dyeings that are photochemically and thermally stabilised in the practice of this invention are those produced with acid or metal complex dyes, typically 1:2 chromium, 1:2 cobalt or copper complex dyes, and also with disperse and reactive dyes.

Examples of such dyes are listed in the Colour Index, 3rd Edition 1971, Volume 4.

Polyamide fibre material will be understood as meaning in the context of this invention synthetic polyamide, including polyamide 6, polyamide 66 or polyamide 12, as well as modified, e.g. basic dyeable, polyamide. In addition to pure polyamide fibres, polurethane/polyamide blends, for example tricot material made from polyamide/polyurethane in the ratio 70:30, are also suitable. Basically the pure polyamide material or blends thereof may be in any form of presentation, including fibres, yam, woven fabrics, knitted fabrics, nonwovens or pile material.

The process of this invention is particularly suitable for treating polyamide fibre material that is exposed to the influence of light and heat, for example car upholstery or carpets.

The invention is illustrated by the following Examples in which parts and percentages are by weight.

EXAMPLE 1 a) To a neutral solution of 0.025 mol of 2-(2,4-dichloro-s-triazin-6-ylamino)benzene-1,4-disulfonic acid in 90 ml of water are added 2.13 g of piperidine, whereupon the pH rises to above 9, but rapidly fails again. The pH is finally kept at 7 by the dropwise addition of a 15% solution of sodium carbonate, and the reaction mixture is smultaneously warmed to 38°–41° C. The reaction mixture is stirred until the condensation is complete.

b) To the above solution are rapidly added 5.31 g of 4-butylamino-2,2,6,6-tetramethyl-piperidine and the reaction temperature is raised to 85°–89° C. The reaction mixture is stirred for 17 hours, then cooled to 10° C., acidified to pH 4 with 2M hydrochloric acid and the product is then salted out with 18 g of NaCl in four portions. The precipitate is isolated by filtration, washed with 50 ml of a 10%, and 25 ml of a 1%, solution of sodium chloride and dried under vacuum at 80° C., giving a powder of formula

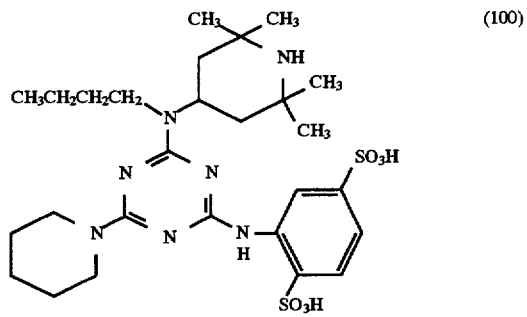

(100)

EXAMPLE 2 a) To a neutral solution of 0.05 mol of 2-(2,4-dichloro-s-triazin-6-ylamino)benzene-1,4-di-sulfonic acid in 150 ml of water are added 4.65 g of aniline. With stirring, the reaction mixture is warmed to 35° C. while keeping the pH at 7 by the simultaneous dropwise addition of 2M aqueous sodium hydroxide. Stirring is continued until the condensation is complete and no more aniline can be detected.

b) To the above solution are added 10.61 g of 4-butylamino-2,2,6,6-tetramethylpiperidine and the reaction mixture is heated to 85° C. and kept at this temperature for 20 hours. The contents of the flask are cooled to 40° C., acidified to pH 5 with 2M hydrochloric acid and the product is then salted out with mit 40 g of NaCl. The precipitate is isolated by filtration, washed in portions with 60 ml of a 15% solution of sodium chloride and dried under vacuum at 70° C., giving a powder of formula

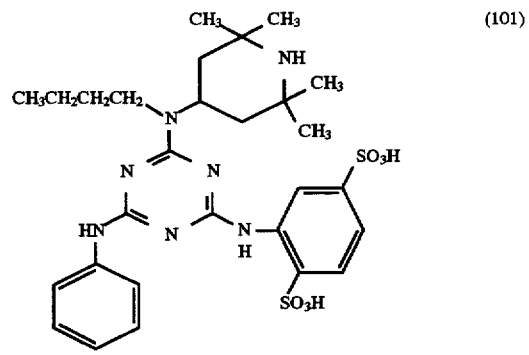

(101)

EXAMPLE 3

The procedure of Example 2 is repeated, but replacing in step b) 10.61 g of 4-butylamino-2,2,6,6-tetramethylpiperidine with 7.88 g of 4-amino-2,2,6,6-tetramethylpiperidine, giving a compound of formula

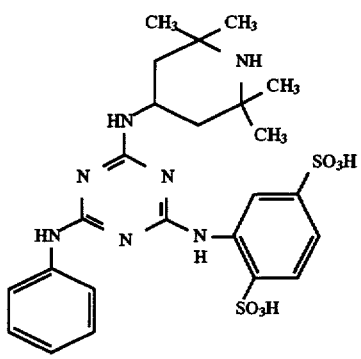 (102)

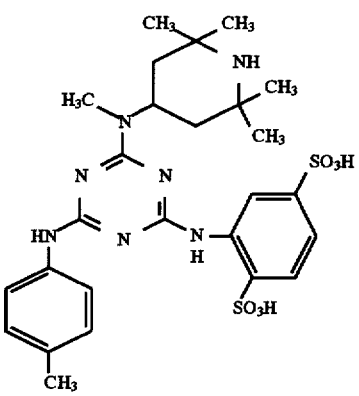 (104)

EXAMPLE 4 a) A solution of 10.7 g of p-toluidine in 50 ml of dioxane is added dropwise over 20 minutes to a solution of 0.1 mol of 2-(2,4-dichloro-s-triazin-6-ylamino)benzene-1,4-disulfonic acid in 300 ml of water, while keeping the pH at c. 7 by the simultaneous dropwise addition of a 15% solution of sodium carbonate. The reaction mixture is stirred for 1 hour at 35° C. to bring the reaction to completion. The contents of the flask are then cooled to room temperaure and the reaction solution is divided into 3 equal portions.

b) 5.2 g of 4-amino-2,2,6,6-tetramethylpiperidine are added rapidly to one portion of the above solution and the reaction temperature is raised to 80°–85° C. The reaction mixture is stirred for 16 hours, cooled to 10° C., and acidified with 2M hydrochloric acid to pH 3. To the reaction mixture are then added 50 ml of a 10% solution of sodium chloride. The precipitate is isolated by filtration, washed with a small amount of water and dried under vacuum at 70° C., giving a powder of formula

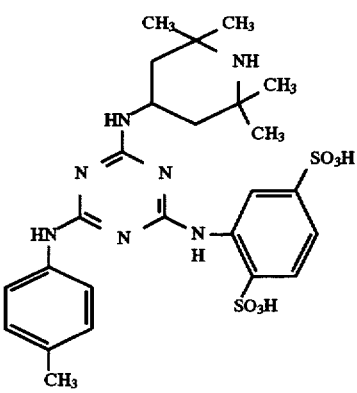 (103)

EXAMPLE 5

The procedure of Example 4b is repeated, but replacing 5.2 g of 4-amino-2,2,6,6-tetramethylpiperidine with 5.6 g of 4-methylamino-2,2,6,6-tetramethylpiperidine, giving a compound of formula

EXAMPLE 6

The procedure of Example 4b is repeated, but replacing 5.2 g of 4-amino-2,2,6,6-tetramethylpiperidine with 5.6 g of 4-butylamino-2,2,6,6-tetramethylpiperidine, giving a compound of formula

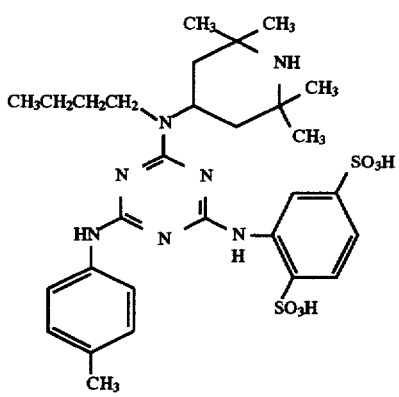 (105)

The following compounds can also be prepared by procedures analogous to those described in Examples 1 to 6:

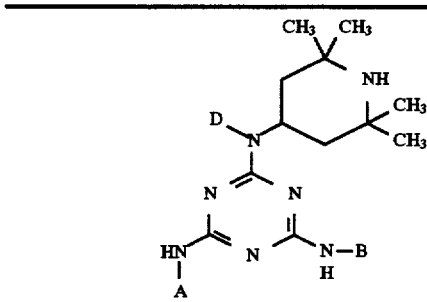

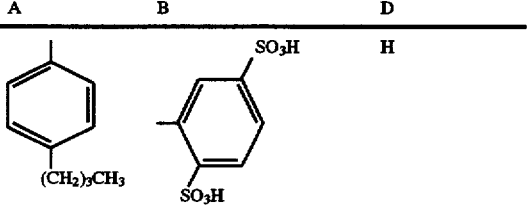

| No. | A | B | D |
|---|---|---|---|
| 106 | (phenyl with CH₃) | (phenyl with SO₃H and SO₃H, (CH₂)₃CH₃) | H |

-continued

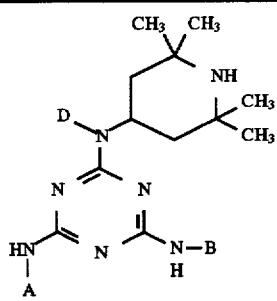

| No. | A | B | D |
|-----|---|---|---|
| 107 | 4-C(CH₃)₃-phenyl | 2,4-(SO₃H)₂-phenyl | H |
| 108 | 4-C(CH₃)₃-phenyl | 2,4-(SO₃H)₂-phenyl | —(CH₂)₃CH₃ |
| 109 | 4-CH₃-phenyl | 2,4-(SO₃H)₂-phenyl | —(CH₂)₃CH₃ |
| 110 | 4-CH₃-phenyl | 2-Cl-3,5-(SO₃H)₂-phenyl | —(CH₂)₃CH₃ |
| 111 | 4-CH₃-phenyl | 2-CH₃-3,5-(SO₃H)₂-phenyl | —(CH₂)₃CH₃ |
| 112 | 4-CH₃-phenyl | 2-OH-3,5-(SO₃H)₂-phenyl | —(CH₂)₃CH₃ |
| 113 | 4-CH₃-phenyl | 2,5-(CH₃)-3-SO₃H-phenyl | —(CH₂)₃CH₃ |

-continued

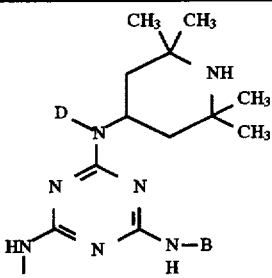

| No. | A | B | D |
|-----|---|---|---|
| 114 | 4-CH₃-phenyl | 2-CH₂CH₃-4-SO₃H-phenyl (with SO₃H) | —(CH₂)₃CH₃ |

EXAMPLE 7

A 10 g sample of polyamide 6 knitted fabric is dyed in a ®AHIBA dyeing machine at a liquor to goods ratio of 1:30. The dye liquor cntains the following ingredients: 0.5 g/l of monosodium phosphate, 1.5 g/l of disodium phosphate, 0.04% by weight of the dye of formula (I), 0.002% by weight of the dye of formula (II) and 0.001% of the dye of formula (III) (the percentages are in each case based on the material to be dyed) in dissolved form:

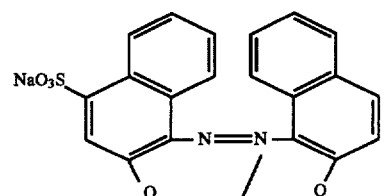

(I)

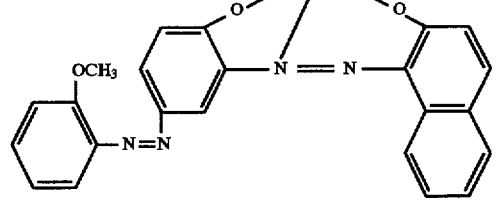

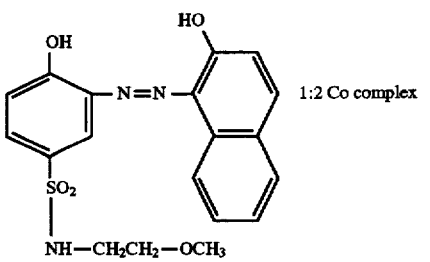

(II) 1:2 Co complex (III) a 1:2 Co mixed complex consisting of

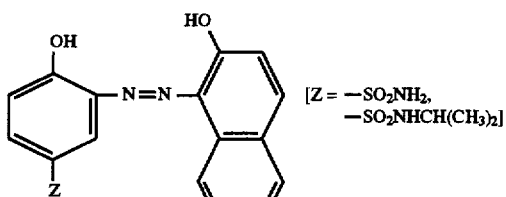

and

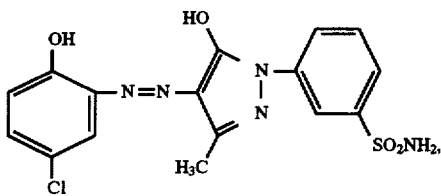

as well as 0.25%, based on the goods to be dyed, of the compound of formula (102)

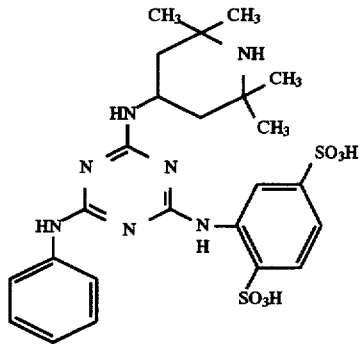

The liquor is heated to 45° C. After addition of the textile material, treatment is carried out for 10 minutes at this temperature and the dyebath is heated to 95° C. at a rate of 2° C./minute. After a dyeing time of 15 minutes at 95° C., 2% by weight of 80% acetic acid, based on the material to be dyed, is added, and dyeing is carried out for another 30 minutes. The dyebath is afterwards cooled to 60° C., and the dyed material is rinsed with hot water and dried.

Dyeings having very good lightfastness properties are obtained.

What is claimed is:

1. A water-soluble triazine of formula

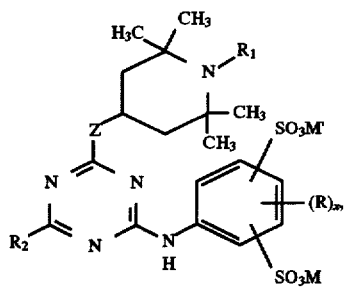

wherein

R is hydrogen, hydroxy, halogen, $C_1-C_5$alkyl which is unsubstituted or substituted by carboxy, $C_1-C_5$alkoxy, $C_1-C_5$alkanoyl, benzoyl, mono- or di-$C_1-C_5$alkanoylamino, carboxy, carbamoyl, phenylsulfonyl which is unsubstituted or substituted by $C_1-C_5$alkyl or halogen, phenoxy which is unsubstituted or substituted by $C_1-C_5$alkyl or halogen, phenylthio which is unsubstituted or substituted by $C_1-C_5$alkyl or halogen or styryl which is unsubstituted or substituted by $C_1-C_5$alkyl or halogen, $R_1$ is hydrogen, oxyl, hydroxy, $C_1-C_5$alkyl, $C_2-C_5$alkenyl, $C_1-C_5$alkoxy, $C_1-C_5$alkanoyl, benzoyl or benzyl $R_2$ is mono-$C_1-C_5$alkylamino, di-$C_1-C_5$-alkylamino, phenyl-$C_1-C_5$-alkylamino, cycloalkylamino or phenylamino, Z is —O— or —(NR$_3$)—, wherein $R_3$ is hydrogen or $C_1-C_5$alkyl, M and M' are each independently of the other hydrogen, an alkali metal cation, an alkaline earth metal cation or an ammonium cation or an organic ammonium cation of formula $(C_1-C\text{ alkyl})_n(H)_mN^+$, m is 0 to 3, n is 1 to 4, and the sum of m+n=4, and X is 1 or 2.

2. A water-soluble triazine according to claim 1, wherein R is hydrogen, halogen, hydroxy or $C_1-C_5$alkyl.

3. A water-soluble triazine according to claim 1, wherein $R_1$ is hydrogen or $C_1-C_5$alkyl.

4. A water-soluble triazine according to claim 1, wherein Z is —(NR$_3$)—, wherein $R_3$ is hydrogen or $C_1-C_5$alkyl.

5. A water-soluble triazine according to claim 1, wherein the two substituents —SO$_3$M and —SO$_3$M' are in positions 2 and 5 at the benzene ring, relative to the amino group.

6. A water-soluble triazine according to claim 1, wherein R is hydrogen, halogen, hydroxy or $C_1-C_5$alkyl, $R_1$ is hydrogen or $C_1-C_5$alkyl, $R_2$ is mono-$C_1-C_5$alkylamino, di-$C_1-C_5$alkylamino, phenyl-$C_1-C_5$alkylamino, cycloalkylamino or phenylamino which is unsubstituted or substituted in the phenyl moiety by $C_1-C_5$alkyl, and Z is —(NR$_3$)—, and the two substituents —SO$_3$M and —SO$_3$M' are located at the benzene ring in positions 2 and 5 relative to the amino group.

7. A water-soluble triazine according to claim 1, wherein R is hydrogen, halogen, hydroxy, methyl or ethyl, $R_1$ is hydrogen, $R_2$ is piperidino or phenylamino which is unsubstituted or substituted in the phenyl moiety by $C_1-C_5$alkyl, and Z is —(NR$_3$)—, wherein $R_3$ is hydrogen, methyl or butyl, and the two substituents —SO$_3$M and —SO$_3$M' are located at the benzene ring in positions 2 and 5 relative to the amino group.

8. A process for the preparation of a triazine of formula

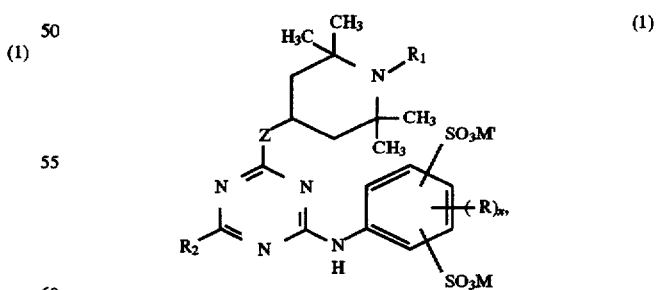

wherein

R is hydrogen, hydroxy, halogen, $C_1-C_5$alkyl which is unsubstituted or substituted by carboxy, $C_1-C_5$alkoxy, $C_1-C_5$alkanoyl, benzoyl, mono- or di-$C_1-C_5$alkanoylamino, carboxy, carbamoyl, phenylsulfonyl which is unsubstituted or substituted by $C_1-C_5$alkyl or halogen, phenoxy which is unsubstituted or substituted by $C_1$–$C_5$alkyl or halogen, phenylthio which is unsubstituted or substituted by $C_1$–$C_5$alkyl or halogen or styryl which is unsubstituted or substituted by $C_1$–$C_5$alkyl or halogen, $R_1$ is hydrogen, oxyl, hydroxy, $C_1$–$C_5$alkyl, $C_2$–$C_5$alkenyl, $C_1$–$C_5$alkoxy, $C_1$–$C_5$alkanoyl, benzoyl or benzyl, $R_2$ mono-$C_1$–$C_5$alkylamino or di-$C_1$–$C_5$alkylamino, phenyl-$C_1$–$C_5$alkylamino, cycloalkylamino or phenylamino Z is —O— or —(NR$_3$)—, wherein $R_3$ is hydrogen or $C_1$–$C_5$alkyl, M and M' are each independently of the other hydrogen, an alkali metal cation, an alkaline earth metal cation or an ammonium cation or an organic ammonium cation of formula $(C_1\text{-}C_4\text{alkyl})_n(H)_mN^+$, m is 0 to 3, n is 1 to 4, and the sum of m+n=4, and x is 1 or 2, which process comprises reacting 1 mol of a 2,4,6-trihalo-s-triazine, in succession, with 1 mol of the compound of formula

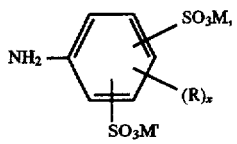

wherein M, M', Z, R and x are as defined with respect to formula (1), and with 1 or 2 mol of the piperidine of formula

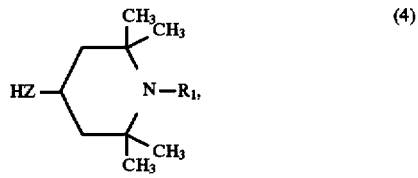

wherein $R_1$ and Z are as defined with respect to formula (1) and, if only 1 mol of the piperidine of formula (4) is used with 1 mol of a $C_1$–$C_5$alkanolate, cycloalkanolate, phenolate, $C_1$–$C_5$alkylthiolate, cycloalkylthiolate or a phenylthiolate, a mono-$C_1$–$C_5$alkylamine, di-$C_1$–$C_5$alkylamine, cycloalkylamine, phenylamine, a 1-azacycloalkyl or morpholino compound, the sequence of the individual reaction steps is in any order.

* * * * *